United States Patent [19]

Cheney et al.

[11] Patent Number: 5,351,697
[45] Date of Patent: Oct. 4, 1994

[54] THREE-DIMENSIONAL IMPEDANCE IMAGING PROCESS

[75] Inventors: Margaret Cheney, Troy; David Isaacson, Latham, both of N.Y.

[73] Assignee: Rensseleaer Polytechnic Institute, Troy, Mich.

[21] Appl. No.: 128,834

[22] Filed: Sep. 29, 1993

Related U.S. Application Data

[63] Continuation-in-part of Ser. No. 808,795, Dec. 16, 1991, Pat. No. 5,284,142.

[51] Int. Cl.$^5$ ............................................... A61B 5/05
[52] U.S. Cl. .................................. 128/734; 364/413.13
[58] Field of Search .................... 128/734; 364/413.13

[56] References Cited

U.S. PATENT DOCUMENTS 4,486,835 12/1984 Bai et al. .......................... 128/734 X
5,184,624 2/1993 Brown et al. ...................... 128/734
5,272,624 12/1993 Gisser et al. .................... 128/734 X

*Primary Examiner*—Ruth S. Smith
*Attorney, Agent, or Firm*—Notaro & Michalos

[57] ABSTRACT

A method for obtaining sets of current patterns for three-dimensionally imaging the interior of a body having an internal resistivity using electrical impedance tomography comprises providing an array of electrodes arranged in a plurality of groups for an impedance imaging system. A linearly independent set of current patterns is also established for forming a basis for each group. A constant pattern is then adjoined to each basis for forming an augmented basis for each group. A tensor product is then taken of the augmented basis for forming a tensor product basis. Finally, the constant pattern from the tensor product basis is removed in order to establish a basis of current patterns for being applied to the array of electrodes.

4 Claims, No Drawings

THREE-DIMENSIONAL IMPEDANCE IMAGING PROCESS

CROSS-REFERENCE TO RELATED APPLICATION

The present application is a continuation-in-part application of Ser. No. 07/808,795, filed Dec. 16, 1991 entitled "THREE-DIMENSIONAL IMPEDANCE IMAGING PROCESSES", which is incorporated here by reference and now U.S. Pat. No. 5,284,142.

FIELD AND BACKGROUND OF THE INVENTION

The present invention relates in general to electrical impedance tomography and in particular, to a new and useful method for obtaining sets of current patterns which are used for producing a three-dimensional impedance image of the interior of a body.

The present invention has applications in medical imaging, clinical monitoring, non-destructive evaluation, process control and the imaging of multiphase fluid flow.

Although superficially similar to X-ray computed tomography or positron emission tomography, electrical impedance tomography (EIT) encounters fundamentally different problems when attempting to create an image. In X-ray computer tomography, for example, the paths of photons through the body are essentially straight lines. In contrast, current paths in EIT are functions of an unknown resistivity distribution. This gives rise to a non-linear reconstruction problem.

The physiological basis for EIT, relies on the fact that biological tissues contain free charge carriers that permit them to act as relatively poor electrical conductors. This ability to conduct electricity varies substantially among the various body tissues. Some typical values for resistivity of biological tissues are disclosed in Table 1. The goal of EIT is to compute and display the spatial distribution of resistivity inside the body.

TABLE 1

| Material | Resistivity ($\rho$) ohm-cm |
|---|---|
| Blood | 150 |
| Plasma | 63 |
| Cerebrospinal Fluid | 65 |
| Urine | 30 |
| Skeletal muscle | 300 |
| Cardiac muscle | 750 |
| Lung | 1275 |
| Fat | 2500 |
| Copper | $1.724 \times 10^{-6}$ |

The present invention is related to the subject matter of U.S. Pat. No. 4,920,490 issued to one of the co-inventors of the present application and incorporated here by reference.

This invention is also related to U.S. patent application Ser. No. 07/727,075 entitled A LAYER STRIPPING PROCESS FOR IMPEDANCE IMAGING, which is also incorporated here by reference and which discloses mathematical theories and manipulations which are useful in understanding the present invention. For additional disclosure concerning hardware useful in practicing the present invention, see U.S. patent application Ser. No. 07/734,591 entitled CURRENT PATTERNS FOR ELECTRICAL IMPEDANCE TOMOGRAPHY which is also incorporated here by reference.

Additionally, the present invention relates to trigonometric current patterns such as those described by Cheney et al., NOSER: An Algorithm For Solving the Inverse Conductivity Problem, 2 Int'l. J. Imaging Systems and Technology, 66–75 (1990).

The present invention also relates to Walsh function patterns such as those disclosed by U.S. patent application Ser. No. 07/591,615 entitled CURRENT PATTERNS FOR IMPEDANCE TOMOGRAPHY, now U.S. Pat. No. 5,272,624, which is incorporated herein by reference.

SUMMARY OF THE INVENTION

The present invention pertains to a method for obtaining sets of current patterns for three-dimensionally imaging the interior of a body having an internal resistivity using electrical impedance tomography. The method according to the present invention utilizes various current patterns such as trigonometric current patterns and Walsh function patterns for application to an impedance imaging system.

According to the present invention, the method comprises providing an array of electrodes arranged in a plurality of groups for an impedance imaging system. A current for each electrode in the groups is provided for establishing a current pattern. After which, a linearly independent set of current patterns is also established for forming a basis for each group. A constant pattern is then adjoined to each basis for forming an augmented basis for each group. A tensor product is then taken of the augmented basis for forming a tensor product basis. Finally, the constant pattern from the tensor product basis is removed in order to establish an applied basis of current patterns for being applied to the array of electrodes.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

The present invention provides a method for obtaining useful sets of current patterns which are used for three-dimensional imaging systems for imaging the interior of a body having an internal resistivity using electrical impedance tomography.

The present invention is applicable to various imaging systems. For illustration purposes, suppose an impedance imaging system has L electrodes arranged in an array with M rows and N columns, where $M \times N = L$. A "current pattern" is defined as a set of L currents, one for each electrode. A "basis" of current patterns is a linearly independent set of current patterns that has the property that every possible current pattern can be written as a linear combination of these basis patterns. A basis of current patterns contains $L-1$ current patterns. That is, L, the number of electrodes, minus one, is the basis of current patterns.

The present invention provides a method for systematically selecting current patterns as a basis which are then applied to a full array of electrodes.

The first step is to choose a basis of current patterns for a linear arrangement of M electrodes. For example, such a basis could be a set of trigonometric current patterns or a set of Walsh function patterns. The second step is to choose a basis of current patterns for a linear arrangement of N electrodes. The third step is to adjoin the constant pattern to each basis. The constant pattern is not an allowed pattern for a simple linear arrangement, because the current being injected is not being extracted anywhere. The resulting basis is the "augmented" basis. The fourth step is to take the product of each pattern in the first augmented basis with every pattern in the second augmented basis. The resulting set of patterns is the "tensor product" of the augmented bases. The patterns in the tensor product are possible patterns for the M×N array of electrodes. The fifth and final step is to delete the constant pattern (which arises from multiplying together the two constant patterns, one from each augmented basis) from the tensor product of the augmented basis. The resulting set of patterns is a basis for the M×N array.

By way of example, suppose there are three electrodes in the horizontal direction, i.e. first group of electrodes, and two electrodes in the vertical direction, i.e. second group of electrodes. Both groups constituting a full array of electrodes.

The first step is to choose a basis for the three-electrode array which may be $\{(1,-1,0), (1,0,-1)\}$. The first current pattern, $(1,-1,0)$, corresponds to applying 1 mA on the first electrode, $-1$ mA on the second electrode, and no current on the third electrode. A second current pattern, $(1,0,-1)$, corresponds to applying 1 mA on the first electrode, no current on the second electrode, and $-1$ mA on the third electrode.

Any other current pattern on the three electrodes can be expressed as a linear combination of these two current patterns listed above. For example, the pattern $(0,-2,2)$ is equal to $$2*(1,-1,0)-2*(1,0,-1).$$

Thus, there can only be two linearly independent patterns because the currents in each pattern must sum to zero, due to the conservation of charge principle.

The second step is to choose a basis of current patterns for the two-electrode array, for instance, $\{(1,-1)\}$.

The third step is to adjoin a constant pattern to each basis for establishing augmented bases. The augmented bases, for the example above, are then $$\{(1,-1,0), (1,0-1), (1,1,1)\}$$

and $$\{(1,-1), (1,1)\}.$$

Note that $(1,1,1)$ is the constant pattern for the first basis and $(1,1)$ is the constant pattern for the second basis.

The fourth step is to take the tensor product of the augmented bases. This results in the basis:

| 1 | −1 | 0 | | 1 | 0 | −1 | | 1 | 1 | 1 |
|---|---|---|---|---|---|---|---|---|---|---|
| −1 | 1 | 0 | | −1 | 0 | 1 | | −1 | −1 | −1 |
| 1 | −1 | 0 | | 1 | 0 | −1 | | 1 | 1 | 1 |
| 1 | −1 | 0 | | 1 | 0 | −1 | | 1 | 1 | 1 |

The fifth and final step is to remove the constant pattern. This deletion gives the final result

| 1 | −1 | 0 | | 1 | 0 | −1 | | 1 | 1 | 1 |
|---|---|---|---|---|---|---|---|---|---|---|
| −1 | 1 | 0 | | −1 | 0 | 1 | | −1 | −1 | −1 |
| 1 | −1 | 0 | | 1 | 0 | −1 | | | | |
| 1 | −1 | 0 | | 1 | 0 | −1 | | | | |

In accordance with the present invention, the final basis is a basis of $3*2-1=5$ current patterns that can be applied to the full 3 by 2 electrode array. In order to produce an image, one must apply all five of these current patterns (one after the other), measure the corresponding voltage patterns, and use all this data to make an image in a manner taught in one or more of the above-identified applications which are incorporated here by reference.

The requirement, according to the present invention, of obtaining linear independence of a set of vectors, can be found, for example, in the reference *Introduction to Linear Algebra With Applications*, Friedberg et al., Prentice-Hall, pgs. 132–136.

Although the present invention relies heavily on mathematical manipulations, it is more than simply an algorithm and more than simply utilizing an algorithm in a particular technological environment. The present invention, does not preempt an algorithm, but instead defines a method of first obtaining sets of currents and then applying the obtained sets of currents to a multidimensional array of electrodes for the purpose of creating an EIT image. The method of applying currents to electrodes, followed by reading voltages resulting from those applied currents and thereafter creating an image using the voltages, is statutory subject matter and the method of the present invention provides an advancement in the field of EIT which is both useful and advantageous.

Another more general example of forming the tensor product of two current patterns, which is part of the present invention, can be expressed as follows.

The M×N array of electrodes are positioned:

| (1,1) | (1,2) | (1,3) | (1,4) |
|---|---|---|---|
| (2,1) | (2,2) | (2,3) | (2,4) |
| (3,1) | (3,2) | (3,3) | (3,4) |
| (4,1) | (4,2) | (4,3) | (4,4) |
| (5,1) | (5,2) | (5,3) | (5,4) |

Suppose a current pattern in the horizontal direction is (A, B, C, D) and a current pattern in the vertical direction is:

a
b
c
d
e.

Then the corresponding tensor product pattern for the full array would be:

| Aa | Ba | Ca | Da |
|---|---|---|---|
| Ab | Bb | Cb | Db |
| Ac | Bc | Cc | Dc |
| Ad | Bd | Cd | Dd |
| Ae | Be | Ce | De. |

If, for example, A=2 mA and d=−3 mA, then the current on electrode (4,1) would be Ad=−6 mA.

The current pattern in the horizontal direction is (A=2, B=0, C=−2, D=0), and the current pattern in the vertical direction is (a=0, b=1, c=0, d=−3, e=2) where all numbers are in milliamps. Then the tensor product of these two current patterns would be:

| | | | |
|---|---|---|---|
| 0 | 0 | 0 | 0 |
| 2 | 0 | −2 | 0 |
| 0 | 0 | 0 | 0 |
| −6 | 0 | 6 | 0 |
| 4 | 0 | −4 | 0. |

Note that this would be only one current pattern in the required basis of 4*5−1=19 patterns. A second, linearly independent pattern could be constructed from (A=0, B=1, C=0, D=−1) and (a=1, b=0, c=−2, d=0, e=1). The tensor product of these two is:

| | | | |
|---|---|---|---|
| 0 | 1 | 0 | −1 |
| 0 | 0 | 0 | 0 |
| 0 | −2 | 0 | 2 |
| 0 | 0 | 0 | 0 |
| 0 | 1 | 0 | −1. |

To provide an better intuitive basis for explaining what is meant by linearly independent sets of current patterns, and in addition to the above-identified standard reference concerning linear algebra, a set of vectors is linearly independent if it is not possible to express one of the vectors in term of the others.

For example, the set of vectors {(1,0,0), (0,1,0), (0,0,1)} is linearly independent, but the set of vectors {(1,0,0), (0,1,0), (1,1,0)} is not, because the sum of the first two in the set, equals the third.

The phrase "adjoining the constant pattern" in the present application means to include the constant pattern into the set of basis vectors. For example, if we denote the constant vector by C, and if the original basis vectors are A1, A2, A3, then the augmented basis would be {A1, A2, A3, C}.

Further, explaining the fifth step of the invention, assume the original two bases are {A1, A2, A3} and {B1, B2, B3}. After adjoining the constant pattern C1 to the first basis and the constant pattern C2 to the second basis, the two bases would be {A1, A2, A3, C1} and {B1, B2, B3, C2}. Different letters are used for the two constant patterns because they might be vectors with different numbers of entries. After taking the product, one of the product vectors, namely (C1)(C2), will be the product of the two constant patterns, which will itself be a constant pattern. For example, suppose one electrode array has 3 electrodes and the other has 2.

Then a constant pattern (C1) for the 3-electrode array would be (1 mA, 1 mA, 1 mA); a constant pattern (C2) for the 2-electrode array would be (1 mA, 1 mA). Note, however, that these patterns violate the conservation of charge, and cannot actually be applied. The pattern (C1)(C2) would, however, be

| | | |
|---|---|---|
| 1mA | 1mA | 1mA |
| 1mA | 1mA | 1mA. |

This pattern also violates conservation of charge, which is why we need to remove it from the tensor product basis for the full array.

While a specific embodiment of the invention has been shown and described in detail to illustrate the application of the principles of the invention, it will be understood that the invention may be embodied otherwise without departing from such principles.

We claim:

1. A method for electrical impedance imaging by obtaining and using sets of current patterns for three-dimensionally imaging the interior of a body having an internal resistivity using electrical impedance tomography, the method comprising:

providing a multidimensional array of electrodes arranged in a plurality of groups for an impedance imaging system;

establishing a linearly independent set of current patterns for forming a basis for each group;

adjoining a constant pattern to each basis for forming an augmented basis for each group;

taking the tensor product of the augmented bases for forming a tensor product basis for each group;

removing the constant pattern from the tensor product basis for establishing a basis of current patterns for being applied to the array of electrodes;

applying the current patterns to the electrodes to form voltage patterns at the electrodes; and measuring the voltage patterns to create an electrical impedance image of the body.

2. The method according to claim 1, including selecting the current patterns to be trigonometric patterns.

3. The method according to claim 1, including selecting the current patterns to be Walsh patterns.

4. A method according to claim 1, including selecting the array to be a matrix of electrodes, some of the plurality of groups comprising rows of electrodes in the matrix and others of the plurality of groups comprising columns of electrodes in the matrix.

* * * * *

UNITED STATES PATENT AND TRADEMARK OFFICE
CERTIFICATE OF CORRECTION

PATENT NO. : 5,351,697

DATED : October 4, 1994

INVENTOR(S) : Margaret Cheney. et al.

It is certified that error appears in the above-identified patent and that said Letters Patent is hereby corrected as shown below:

On the title page: Item [73]  change "Troy, Mich." to -- Troy, New York--.

Signed and Sealed this

Twentieth Day of December, 1994

*Attest:*

BRUCE LEHMAN

*Attesting Officer*   *Commissioner of Patents and Trademarks*